(12) United States Patent
Josel et al.

(10) Patent No.: US 8,962,338 B2
(45) Date of Patent: Feb. 24, 2015

(54) METHODS FOR MEASUREMENT OF CALCIUM IONS

(71) Applicant: Roche Diagnostics Operations, Inc., Indianapolis, IN (US)

(72) Inventors: Hans-Peter Josel, Weilheim (DE); Hans-Joachim Kytzia, Schallstadt (DE); Matthias Muecke, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/630,665

(22) Filed: Sep. 28, 2012

(65) Prior Publication Data

US 2013/0023055 A1    Jan. 24, 2013

Related U.S. Application Data

(63) Continuation of application No. PCT/EP2011/054713, filed on Mar. 28, 2011.

(30) Foreign Application Priority Data

Mar. 30, 2010  (EP) .................................. 10003408

(51) Int. Cl.
- *G01N 21/75* (2006.01)
- *G01N 33/84* (2006.01)
- *C07C 229/18* (2006.01)

(52) U.S. Cl.
CPC .............. *G01N 33/84* (2013.01); *C07C 229/18* (2013.01)
USPC ........................................................... 436/79

(58) Field of Classification Search
CPC ....... G01N 33/84; G01N 31/22; G01N 31/16; G01N 33/1853; C07D 498/08
USPC ........................................................... 436/79
See application file for complete search history.

(56) References Cited

U.S. PATENT DOCUMENTS 4,753,890 A * 6/1988 Smith-Lewis et al. .......... 436/74
4,795,712 A * 1/1989 Toner et al. ..................... 436/74
(Continued)

FOREIGN PATENT DOCUMENTS

| EP | 0432642 A1 | 6/1991 |
| EP | 0594047 B1 | 4/1994 |

(Continued)

OTHER PUBLICATIONS

International Search Report issued Jun. 14, 2011, in Application No. PCT/EP2011/054713, 3 pages.
(Continued)

*Primary Examiner* — Krishnan S Menon
*Assistant Examiner* — Dwan A Gerido
(74) *Attorney, Agent, or Firm* — Stinson Leonard Street LLP

(57) ABSTRACT

Reagents and methods for determination of calcium within a sample. Specific embodiments include a reagent for determination of calcium comprising a mono-nitro substituted BAPTA-type chelator (BAPTA=1,2-bis(2-aminophenoxy) ethane-N,N,N',N'-tetraacetic acid). Methods for accurate determination of calcium in a sample, such as a blood, whole blood, plasma or serum or any other aqueous liquid sample including cerebrospinal fluid, lymph, salivary juice or urine. Embodiments are also useful for clinical diagnoses.

20 Claims, 7 Drawing Sheets

(56) References Cited

U.S. PATENT DOCUMENTS 5,482,866 A * 1/1996 Denton et al. ................. 436/79
6,068,971 A 5/2000 Berry et al.

FOREIGN PATENT DOCUMENTS

JP 2005298444 A 10/2005
WO 2005/053668 A1 6/2005

OTHER PUBLICATIONS

Barth, Andreas et al., "Decarboxylation is a significant reaction pathway for photolabile calcium chelators and related compounds," Photochemical & Photobiological Sciences, 2006, pp. 107-115, vol. 5.

Bett, Isobel M. and Fraser, G. P., "A Rapid Micro-Method for Determining Serum Calcium," Clinica Chimica Acta, 1959, pp. 346-356, vol. 4.

Harrison, Simon M. and Bers, Donald M., "The effect of temperature and iconic strength on the apparent Ca-affinity of EGTA and the analogous Ca-chelators BAPTA and dibromo-BAPTA," Biochimica et Biophysica Acta, 1987, pp. 133-143, vol. 925.

Masino, Laura et al., "Ligand binding and thermodynamic stability of a multidomain protein, calmodulin," Protein Science, 2000, pp. 1519-1529, vol. 9.

Pethig, R. et al., "On the dissociation constants of BAPTA-type calcium buffers," Cell Calcium, 1989, pp. 491-498, vol. 10.

* cited by examiner

METHODS FOR MEASUREMENT OF CALCIUM IONS

CROSS-REFERENCE TO RELATED APPLICATIONS

This application is a continuation of International Application No. PCT/EP2011/054713, filed Mar. 28, 2011, which claims the benefit of European Patent Application No. 10003408.1, filed Mar. 30, 2010, the disclosures of which are hereby incorporated by reference in their entirety.

BACKGROUND OF THE DISCLOSURE

Blood or serum calcium levels may have diagnostic value and/or be valuable for treatment implications. The reference range for calcium ions is very narrow, 2.20 to 2.55 mmol/L, and slight deviations above or below these levels may be diagnostic of several physiological disorders. The two most common diseases associated with hypercalcaemia (elevated serum calcium) are hyperparathyroidism and malignancy, especially when the malignancy has metastasized to the skeleton and caused bone resorption (i.e. local destruction of the bone accompanied by release of calcium from the site of the metastatic lesion). Decreased serum calcium levels (hypocalcaemia) are commonly associated with hypoparathyroidism. About 1% of newborns have significant hypocalcaemia (serum calcium<1.75 mmol/L) with symptoms like irritability, twitching and convulsions which require immediate medical intervention.

Magnesium, like calcium, is a major element found in the body. Impairments in the level of magnesium also lead to clinical symptoms some of which are very similar to the ones found with impaired levels of calcium. Given the nearly identical clinical symptoms of low serum calcium and low serum magnesium, it can be imperative to delineate which element is causing the clinical symptoms. As such, often both serum calcium and magnesium measurements are necessary to determine which element or as the case may be whether both elements are out of normal range. Further, in some cases quantification of the magnesium may interfere with the quantification of calcium.

Currently, the reference method for measuring calcium and magnesium is atomic absorption. However, for routine measurements, atomic absorption is somewhat inconvenient, requiring expensive instrumentation and a rather skilled operator to perform the assays in order to achieve sufficient precision and reproducibility.

BRIEF SUMMARY OF THE DISCLOSURE

The present disclosure provides reagents and methods for quantitatively measuring calcium in analytical samples. The methods described herein utilize a chelator that a) is stable under storage conditions and on board of an analyzer, b) does not contain toxic elements (for example, arsenic), c) has a relatively low reagent blank absorbance, d) does not bind to magnesium ions or other metal ions (for example, gadolinium), e) allows for rapid determinations and high sample throughput, and f) leads to a precise measurement of calcium ions over a broad measuring range.

According to the surprising and unexpected results disclosed herein, the methods provided herein disclose mono-nitro-derivatives of BAPTA-type chelators exhibiting advantageous and unexpected properties rendering them very appropriate for measurement of calcium ions.

The present disclosure relates to a reagent for determination of calcium and to a determination method using that reagent. More particularly, it relates to a reagent for determination of calcium comprising a mono-nitro substituted BAPTA-type chelator (BAPTA=1,2-bis(2-aminophenoxy) ethane-N,N,N',N'-tetraacetic acid). A determination method which permits accurate determination of calcium in a sample, such as a blood sample (e.g. whole blood, plasma or serum) or any other aqueous liquid sample (e.g. cerebrospinal fluid, lymph, salivary juice or urine) and thus is especially useful for clinical diagnoses as described.

The present disclosure provides a reagent that is very useful in the measurement of calcium ions and amongst other positive aspects, has excellent storage stability, is free from the problem of environmental pollution by arsenic, does not show interference by magnesium or gadolinium and permits rapid and accurate calcium determination over a broad range of concentrations.

The present disclosure relates to a method for determining the concentration of calcium ions in a sample, the method comprising the steps of mixing the sample with a solution comprising a mono-nitro-BAPTA-type chelator thereby binding calcium ions to the mono-nitro-BAPTA-type chelator, releasing calcium ions from the mono-nitro-BAPTA-type chelator, wherein said release causes a change in absorbance of the mono-nitro-BAPTA-type chelator, measuring the change in absorbance and using the change in absorbance measured for determining the concentration of calcium ions.

Also disclosed is a stable reagent composition for measurement of calcium containing a mono-nitro-BAPTA-type chelator and having a pH ranging from pH 8.5 to pH 11.5.

Further the present disclosure is directed to a kit comprising a reagent composition for measurement of calcium having a pH ranging from pH 8.5 to pH 11.5 and containing a mono-nitro-BAPTA-type chelator.

According to an exemplary embodiment of the instant disclosure, a method of measuring calcium ion concentration in a sample is provided. Embodiments of the method include steps of mixing a sample with a solution thereby forming a mixture, the solution comprising a compound having a chemical structure represented by Formula I

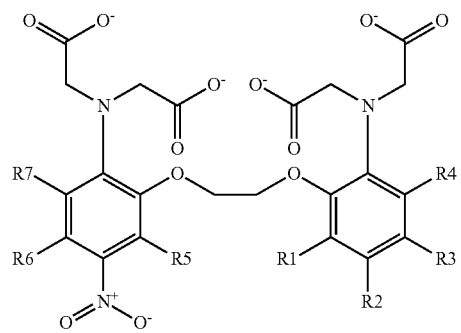

wherein R1 is selected from the group consisting of hydrogen, halogen, carboxy, alkyl and formyl; R2 is independently selected from the group consisting of hydrogen, halogen, alkyl, alkoxy, morpholino, CN, carboxy and formyl; R3 is independently selected from the group consisting of hydrogen, halogen, N-alkyl sulfate, carboxy, alkoxy, phenyl, CN, CF3, and tertiary butyl; R4 is independently selected from the group consisting of hydrogen, halogen or alkyl; R5 and R7 are independently selected from the group consisting of hydrogen or alkyl; R6 is selected from group consisting of hydrogen, alkyl, alkoxy and halogen; or wherein R3 and R4 form an aromatic bridge, and the solution further comprising a positively charged counter ion. Methods further include the steps of incubating the mixture for a period of time, whereby calcium ions within the sample bind to the compound and measuring a baseline absorbance value of the mixture. Further, methods also include the steps of adding a releasing agent to the mixture, incubating the mixture of the sample, the solution, and the releasing agent for a period of time, whereby calcium ions release from the compound and measuring a second absorbance value of the mixture of the sample, the solution, and the releasing agent. Such methods also include the steps of calculating a difference in the baseline absorbance value and the second absorbance value, and determining a concentration of calcium ions within the sample based on said step of calculating.

According to other exemplary embodiments of the instant disclosure, a reagent for measuring calcium ion concentration in a sample is provided. In exemplary embodiments, the reagent comprises an aqueous solution having a pH between approximately 8.5 to approximately 11.5, a positively charged counter ion, and a compound having a chemical structure represented by Formula I

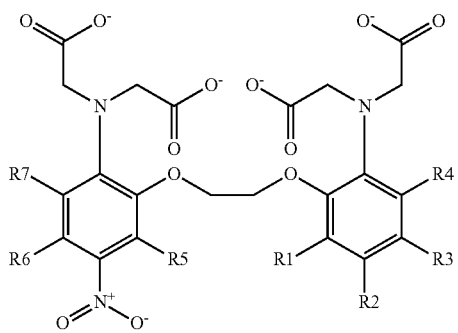

wherein R1 is selected from the group consisting of hydrogen, halogen, carboxy, alkyl and formyl; R2 is independently selected from the group consisting of hydrogen, halogen, alkyl, alkoxy, morpholino, CN, carboxy and formyl; R3 is independently selected from the group consisting of hydrogen, halogen, N-alkyl sulfate, carboxy, alkoxy, phenyl, CN, CF3, and tertiary butyl; R4 is independently selected from the group consisting of hydrogen, halogen or alkyl; R5 and R7 are independently selected from the group consisting of hydrogen or alkyl; R6 is selected from group consisting of hydrogen, alkyl, alkoxy and halogen; or wherein R3 and R4 form an aromatic bridge.

According to some embodiments of the reagent for measuring calcium ions in samples, the reagent may comprise the compound in a concentration ranging from 0.10 mM to 50 mM.

Yet even further embodiments of the instant disclosure include a kit for measuring calcium ion concentration in a sample. In some embodiments, the kit may comprise a reagent comprising an aqueous solution having a pH between approximately 8.5 to approximately 11.5, a positively charged counter ion, and a compound having a chemical structure represented by Formula I

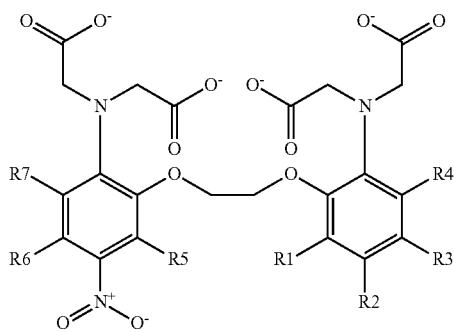

wherein R1 is selected from the group consisting of hydrogen, halogen, carboxy, alkyl and formyl; R2 is independently selected from the group consisting of hydrogen, halogen, alkyl, alkoxy, morpholino, CN, carboxy and formyl; R3 is independently selected from the group consisting of hydrogen, halogen, N-alkyl sulfate, carboxy, alkoxy, phenyl, CN, CF3, and tertiary butyl; R4 is independently selected from the group consisting of hydrogen, halogen or alkyl; R5 and R7 are independently selected from the group consisting of hydrogen or alkyl; R6 is selected from group consisting of hydrogen, alkyl, alkoxy and halogen; or wherein R3 and R4 form an aromatic bridge; and a releasing agent, the releasing agent having a binding constant for calcium ions of log k of at least 7.0 at 20° C.

BRIEF DESCRIPTION OF THE FIGURES

The features of this disclosure, and the manner of attaining them, will become more apparent and the disclosure itself will be better understood by reference to the following description of embodiments of the disclosure taken in conjunction with the accompanying drawing.

Figure 1:
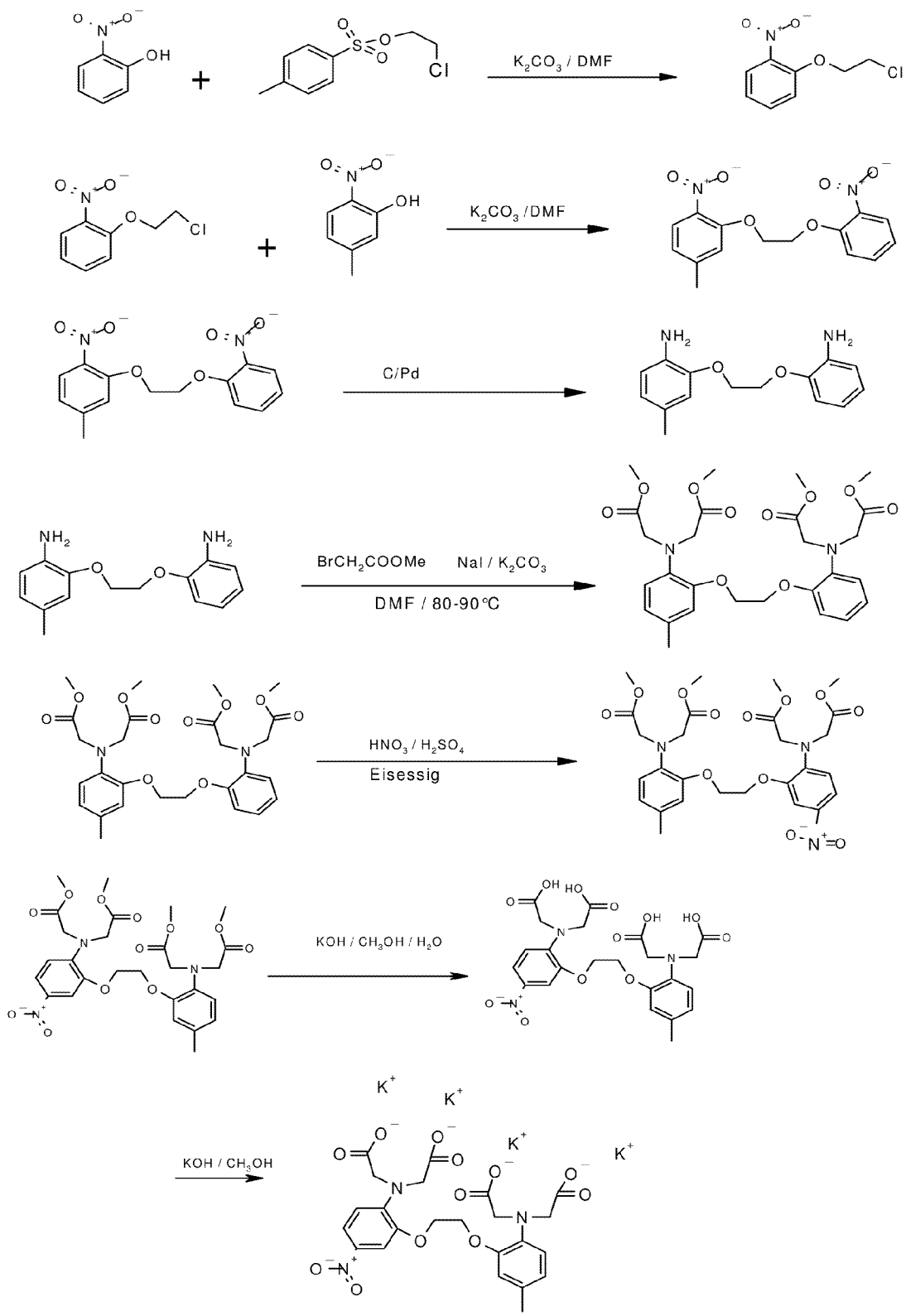
FIG. 1 is a schematic depiction of synthesis of NM-BAPTA.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

In a some embodiments, the present disclosure relates to a method for determining the concentration of calcium ions in a sample, the method comprising the steps of mixing the sample with a solution comprising a mono-nitro-BAPTA-type chelator thereby binding calcium ions to the mono-nitro-BAPTA-type chelator, releasing calcium ions from the mono-nitro-BAPTA-type chelator, wherein said release causes a change in absorbance of the mono-nitro-BAPTA-type chelator, measuring the change in absorbance and using the change in absorbance measured for determining the concentration of calcium ions.

BAPTA-type calcium-chelating agents have been described and used as buffer systems, for example to control the concentration of intracellular calcium ions. Pethig, R. et al., (Cell Calcium 10 (1989) 491-498) have determined the dissociation constants of seven different BAPTA-type calcium buffers.

Catalytic activity of certain enzymes depends on the presence of calcium ions. As described herein, calcium may be quantified, at least in some cases, via a measurement of calcium-dependent enzymatic activity. For example, methods for measurement of calcium ions based on enzymatic procedures have been described in U.S. Pat. No. 6,068,971, the disclosure of which is hereby incorporated by reference in its entirety.

As disclosed herein, a method for determining the concentration of calcium ions in a sample is disclosed, the method comprising the steps of a) mixing the sample with a solution comprising a compound of Formula I

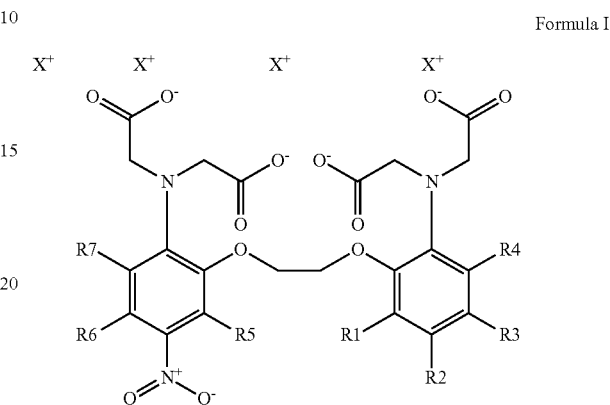

Formula I wherein R1 is selected from hydrogen, halogen, carboxy, alkyl and formyl, R2 is independently selected from hydrogen, halogen, alkyl, alkoxy, morpholino, CN, carboxy and formyl, R3 is independently selected from hydrogen, halogen, N-alkyl sulfate, carboxy, alkoxy, phenyl, CN, CF3, and tertiary butyl, R4 is independently selected from hydrogen, halogen or alkyl, R5 and R7 independently are hydrogen or alkyl R6 is selected from hydrogen, alkyl, alkoxy and halogen, or wherein R3 and R4 form an aromatic bridge and X+, is a positively charged counter ion, thereby binding calcium ions to the compound, b) releasing calcium ions from the compound, wherein said release causes a change in absorbance of the compound, c) measuring the change in absorbance, and d) using the change in absorbance measured in (c) for determining the concentration of calcium ions.

The halogen mentioned as candidate substituent R1, R2, R3, R4 and/or R6 may be selected from Cl— Br— and F—. In some embodiments, the substituent R1 and/or R2, and/or R3 is carboxy. In some embodiments, alkyl as mentioned for R1, R2, R4, R5, R6, and/or R7 may be C1 to C3-alkyl. In some embodiments, alkoxy as mentioned for R2, R3, and/or R6 may be methoxy or ethoxy. Also, according to some embodiments, the aromatic bridge between R3 and R4 may be part of a benzene ring system. Also, in some embodiments, the counter ion X+ may be selected from the group consisting of Na+, K+, Li+ and Cs+. Also, in some embodiments, X+ is K+ or Na+.

As used herein, each of the following terms has the meaning associated with it in this section.

The articles "a" and "an" are used herein to refer to one or to more than one (i.e. to at least one) of the grammatical object of the article. By way of example, "a marker" means one marker or more than one marker. The term "at least" is used to indicate that optionally one or more further objects may be present.

The expression "one or more" denotes 1 to 50, including 1 to 20 also for example 2, 3, 4, 5, 6, 7, 8, 9, 10, 12, or 15.

A compound according to Formula I is capable of binding calcium ions. Upon binding or upon release of calcium a change in its spectral characteristics takes place. This change in spectral characteristics can be easily measured and is directly correlated to the concentration of calcium ions present in a sample.

According to embodiments of the instant disclosure, all calcium ions present in a sample may first be bound to the compound of Formula I prior to being analysed. According a stable base line is obtained. The stable baseline, as described herein, is especially valuable for measuring low concentrations of calcium ions. Upon release of the calcium ions from the compound according to Formula I a measurable change in its spectral characteristics is induced that can be used to exactly determine the concentration of calcium ions present in a sample.

As described and disclosed herein, the compound of Formula I can efficiently bind calcium ions over a broad pH range. Efficient calcium binding can be observed from about pH 5.0 to about pH 11.0. In one embodiment the method according to the present disclosure is practiced under conditions wherein the pH in the assay mixture comprising the compound according to Formula I and the sample is between pH 5.0 and pH 11.0. The reaction mixture contains at least an aliquot of a sample and a compound according to Formula I. In further embodiments the pH in the reaction mixture will be from pH 5.0 or above, from pH 5.5 or above, from pH 6.0 or above from pH 6.5 or to pH 11 or below, also pH 10 or below pH 9.0 or below pH 8.0 or below.

The final concentration for a compound according to Formula I is adjusted to be high enough for reliable measurement of calcium ions in a sample. Due to the high sensitivity achieved by measuring calcium ions using a compound of Formula I, a clinical sample like serum or plasma may be diluted, for example about 100-fold and still be reliably measured. As obvious to the skilled artisan the final concentration of a compound according to Formula I in an assay mixture has to match the final concentration of calcium ions in such assay mixture. In some embodiments the method disclosed will be practiced using a compound according to Formula I in a final concentration that is at least 1.5 fold the expected upper limit for the final concentration of calcium ions.

As mentioned, a sample having 5 mmol/L calcium ions can be reliably measured according to the instant disclosure, this may be the expected upper limit, for example. In case such sample is diluted 1:100 the final concentration of calcium ions in the assay mixture will be 0.05 mmol/L, for example. Accordingly, the final concentration of the compound according to Formula I should be at least 1.5-fold this concentration, i.e. 0.075 mmol/L. Also, the final concentration of a compound according to Formula I in an assay mixture will be at least 2-fold, 2.5-fold, 3-fold and at most 20-fold, 15-fold or 10-fold the calcium ion concentration as calculated for a sample having the expected upper limit of 5 mmol/L. For example, the final concentration of a compound according to Formula I in an assay mixture will be at least 1.5-fold, 2-fold, 2.5-fold, 3-fold and at most 20-fold, 15-fold or 10-fold the molar concentration obtained by multiplying 5 mmol/L with the dilution factor for the sample.

It has been found that long-term stability in solution of a compound according to Formula I is best preserved at a pH of 8.5 or above. In some embodiments, a reagent comprising a compound according to Formula I that does not need to be freshly made or checked frequently for its functionality may be used, therefore in some embodiments, the method according to the present disclosure is practiced with a solution comprising the compound of Formula I having a pH in the range from pH 8.5 to pH 11.5.

In some further embodiments the method according to the present disclosure is performed with a solution comprising the compound of Formula I having a pH in the range from pH 8.5 to pH 11.0 or from pH 9.0 to pH 10.5.

According to some embodiments of the instant disclosure, the method may be practiced with a compound according to Formula I, wherein R1 is either hydrogen or halogen. In some embodiments, the method may be practiced with a compound according to Formula I, wherein R2 of is hydrogen, halogen, carboxy, morpholino or alkyl. In some embodiments of the present disclosure, the method may be practiced with a compound according to Formula I, wherein R3 is hydrogen, halogen, carboxy or alkoxy.

Embodiments of the instant disclosure include a compound according to Formula I capable of binding calcium ions with a binding constant of log k equal to 9.0 or lower. According to embodiments, the binding constant to calcium ions described as log k should be at least 4.0 or higher. In some specific embodiments of the instant disclosure, the binding constant for calcium ions given in log k is between 4.5 and 8.5, for example, between 5.0 and 8.0.

Log k may be measured according to the procedure described in Harrison, S. M. and Bers, D. M., Biochimica et Biophysica Acta 925 (1987) 133-143, the disclosure of which is hereby incorporated by reference in its entirety. According to this method, the calcium binding compound is buffered to pH 7.0 in 25 mM Hepes-buffer. Temperature is kept constant at 20° C. Various concentrations of calcium ions are incubated with a constant amount of calcium binding compound. The fractions of free and bound calcium ions are determined and the affinity constant calculated by aid of a Scatchard plot.

According to some embodiments of the instant disclosure, various combinations of substituents are possible. Such substituents can be chosen and used to influence or modulate the binding constant of a compound according to Formula I. For example, electron-withdrawing groups will lead to a reduced binding constant whereas electron-donating groups in general will result in a stronger binding of calcium ions.

According to some embodiments of the instant disclosure, the substituents to the compound of Formula I are selected to result in a binding constant, given as log k, of 7.0 or less, and for example, a log k between 4.0 and 7.0, of between 4.5 and 6.5 or of between 5.0 to 6.0.

In some embodiments, two or more compounds according to Formula I may be combined in order to perform the method according to the present disclosure. In an exemplary embodiment, a single compound according to Formula I is used.

According to some embodiments of methods disclosed herein, such methods may be based on back-titration (e.g., calcium ions are first bound to the compound of Formula I and released thereafter). The release of calcium ions from the compound according to Formula I is most easily achieved by use of a chelator that binds calcium ions stronger than the compound according to Formula I. In an exemplary embodiment, the chelator used for release of the calcium ions in step b) of the method disclosed herein above has a binding constant that is 10-fold higher as compared to the compound of Formula I used in the method of calcium detection.

Some embodiments of the instant disclosure may include a calcium binding compound according to Formula I with a log k of 5.0 with a chelator having a log k of 6.0. Other embodiments include the use of a chelator having at least a log k of 7.0 or higher. As obvious to the skilled artisan the reagent used to release calcium ions from a compound according to Formula I is best chosen to have spectral characteristics that do not interfere with those of interest (for example, with the absorption or emission spectrum of a compound according to Formula I).

According to some embodiments, the reagent/chelator used for release of calcium from the compounds according to Formula I may be selected from di-, tri-, tetra-acetic acid derivatives, poly-phosphonic acids or phosphoric acid derivatives, 4,4'-Difluoro-BAPTA, 5,5'-Dibromo-BAPTA, 5,5'-Difluoro-BAPTA, 5-Methyl-5'-formyl-BAPTA, 5,5'-dimethyl-BAPTA, (1,2-Cyclohexylenedinitrilo)tetraacetic acid (CETA), citric acid, nitrilotriacetic acid (NTA), iminodiacetic acid (IDA), N-(2-hydroxyethyl)iminodiacetic acid (HIDA), N-(2-Hydroxyethyl)ethylenediamine-N,N',N'-triacetic acid (=HEDTA; CAS 150-39-0, log k=8.14), CyDTA (=CAS 125572-95-4, log k=12.50), TTHA (=CAS 869-52-3, log k=10.06), Me-EDTA (=1,2-Propanediamine-N,N,N',N'-tetraacetic acid, log k=10.4), BAPTA (=CAS 73630-08-7, log K 6.97), DTPA (=Diethylentriaminopentaacetic acid; CAS-Nr.: 67-43-6, log k=10.8), EGTA (=Ethylene glycol-bis(2-aminoethylether)-N,N,N,N-tetraacetic acid; CAS-Nr.: 67-42-5, log k=10.9), DTPMP, (=Diethylentriaminpenta(methylenephosphonic acid); CAS-Nr.: 15827-60-8, log k=10.7) and EDPMP (=Ethylendiamintetra(methylenephosphonic acid); CAS-Nr.: 1429-50-1, log k=10.2).

Also, the method according to the present disclosure may be practiced such that the release of calcium ions is triggered by EDTA, DTPA, EGTA, DTPMP and/or EDPMP.

However, according to methods disclosed herein, the choice of the chelator used to release calcium ions from a compound according to Formula I is not critical, as long as the calcium ions bound to the compound of Formula I are released after addition of such chelator. The concentration of the chelator in the final reaction mixture, according to embodiments of the instant application, will be at least equimolar but not higher than 100-fold the concentration of the compound according to Formula I in this mixture. In some embodiments, it is possible that a surplus of chelator may be used (for example to correct for minor pipetting errors). In other embodiments of methods disclosed herein, the concentration of the chelator in the final reaction mixture is higher than the final concentration for the compound of Formula I (e.g., between 1.5-fold and 50-fold or even between 2-fold and 10-fold).

A reagent used in routine clinical chemistry for measurement of calcium ions should be stable under transport and long term storage conditions. According to the instant disclosure, a compound according to Formula I may not be as stable at acidic or neutral pH as it is under alkaline buffer conditions. Reagent compositions comprising a compound according to Formula I are generally at a pH of approximately 8.5 or higher. In some embodiments the reagent for measurement of calcium ions has a pH ranging from pH 8.5 to pH 11.5, and containing a compound of Formula I as defined in claim 1.

In some embodiments the reagent according to the present disclosure has a pH in the range from pH 8.5 to pH 11.0 or from pH 9.0 to pH 10.5.

Buffer systems that are appropriate to buffer a solution at a pH of 8.5 and/or higher are well-known to the skilled artisan. For example, such buffer system may be selected from AMPD (=2-Amino-2-Methyl-1,3-propanediol), CHES (=2-(N-Cyclohexylamino)-ethanesulfonic acid), AMPSO (=3-[Dimethyl(hydroxylmethyl)-methylamino]-2-hydroxypropanesulfonic acid), CAPSO (=3-Cyclohexylamino)-2-hydroxy-1-propanesulfonic acid), CAPS (=3-Cyclohexylamino)-2-propanesulfonic acid), a glycine buffer system, or a carbonate buffer system. Also the reagent for measurement of calcium ions according to the present disclosure may comprise a buffer system, selected from CAPS or CAPSO.

As disclosed and described herein, calcium concentration in circulation is generally tightly regulated, whereby physiological concentrations are usually between 2.20 to 2.55 mmol/L. Elevated levels of calcium ions in circulation rarely go above 4 mmol/L. As such, reagents according to the instant disclosure should be adapted to measure calcium ions in circulation for covering a measurement range of at least greater than 4 mmol/L, for example up to 5 mmol/L or 5.5 mmol/L. Reagents, according to the instant disclosure for measurement of calcium, should cover the physiologically relevant concentrations. In urine, however, calcium concentrations may vary to a large extent. Thus, some embodiments of the instant disclosure, for example embodiments capable of measuring calcium concentrations in urine, should cover a large measurement range.

In an exemplary embodiment, the reagent for measurement of calcium comprises a compound of Formula I in a concentration ranging from 0.10 mmol/L to 50 mmol/L.

As the skilled artisan will appreciate the final concentration of a compound of Formula I in the assay mixture, comprising the sample to be measured, must match at least the concentration of calcium ions in the sample. In one embodiment the concentration of the compound according to Formula I will be in the range of 0.10 mmol/L to 2 mmol/L. In alternative embodiments the concentration of the compound according to Formula I will be in the range from 0.1, 0.125, 0.15, or 0.2 to 2.0, 1.5 or 1 mmol/L. This reagent can be admixed with the sample to be measured used without further dilution.

In another embodiment a more concentrated reagent for measurement of calcium, based on the compound of Formula I, is provided. Such reagent can be appropriately diluted for measurement of a sample. The concentrated form of a reagent according to the present disclosure may comprise, for example, a compound according to Formula I in a range from 0.5 to 50 mmol/L. In some embodiments the concentration of the compound according to Formula I (in a more concentrated reagent for detection of calcium ions) will be in the range from 0.5, 0.6, 0.7, 0.8, 0.9 or 1 mmol/L to 50, 40, 30, 20, 15, or 10 mmol/L.

In some embodiments, the reagent for measurement of calcium as disclosed in the present disclosure comprises a compound according to Formula I, wherein R1 is either hydrogen or halogen. In some embodiments, the reagent for measurement of calcium as disclosed in the present disclosure comprises a compound according to Formula I, wherein R2 is hydrogen, halogen, carboxy, morpholino or alkyl. In some embodiments, the reagent for measurement of calcium as disclosed in the present disclosure comprises a compound according to Formula I, wherein R3 of Formula I is hydrogen, halogen, carboxy or alkoxy.

According to some embodiments, a detergent may be added to a reagent for measurement of calcium ions for reduction of interfering unspecific binding and/or for the reduction of foam and air bubbles or other positive influences. Thus, some embodiments of the present disclosure include a reagent for measurement of calcium ions having a pH ranging from pH 8.5 to pH 11.5, containing a compound of Formula I (as defined above and herein) and a detergent.

As used herein, the term "detergent" means an ionic or a non-ionic detergent. Examples of detergents include, but are not limited to: sodium dodecyl sulphate (SDS), fatty acid salts, the Triton® family, octyl glycoside, 3-[(3-cholamidopropyl)dimethyl-ammonio]-1-propanesulfonate (CHAPS), sodium dodecyl maltoside (DM), lauryldiethylamine oxide (LDAO), NP-40 and the Tween® family, primary amines, amine acetates and hydrochlorides, quaternary ammonium salts, trimethylethyl ammonium bromide, amides of substituted diamines, diethanolaminopropylamine or diethylaminopropylamide, amides of cyclised diethylenetriamine, alkylaryl sulfonates, petroleum sulfonates, sulfonated glycerides, cholamides, sulfobetaines, alkyl glycosides, saponins, alkyl-polyethylene glycol ethers.

In some embodiments the detergent is a non-ionic detergent. Non-limiting examples of non-ionic detergents are Imbentin V413/91, Thesit, Triton® X-100, Triton® X-114, Brij® 35, Brij® 58, Tween® 20, Tween® 80, Nonidet® P-40, Octyl 13 Glucoside and MEGA 8-Octanoyl-N-methylglucamide. In one embodiment the non-ionic detergent is selected from Brij® 35, Triton® X-100, Tween® 20, and Nonidet® P-40.

In some embodiments of the instant disclosure, reagents for measurement of calcium may be assembled in the form of a kit comprising at least one reagent that contains a calcium indicator, like the compounds currently used or a compound according to Formula I as described in this disclosure. In some embodiments, the present disclosure relates to a test kit for the measurement of calcium, the test kit containing a reagent comprising a compound according to Formula I and having a pH ranging from pH 8.5 to pH 11.5.

In some embodiments of the instant disclosure, kits may include at least two reagents into a kit tailored to measure calcium ions, a first reagent comprising a compound according to Formula I and having a pH ranging from pH 8.5 to pH 11.5.0 and a second reagent comprising a chelator. Some embodiments of the present disclosure relate to a kit containing a first reagent comprising a compound according to Formula I and having a pH ranging from pH 8.5 to pH 11.5 and a second reagent comprising a chelator for calcium ions. Kits may optionally also comprise a package insert and/or one or more additional reagents.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

ILLUSTRATIVE EMBODIMENTS

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A method for determining the concentration of calcium ions in a sample, the method comprising the steps of
   a) mixing the sample with a solution comprising a compound of Formula I

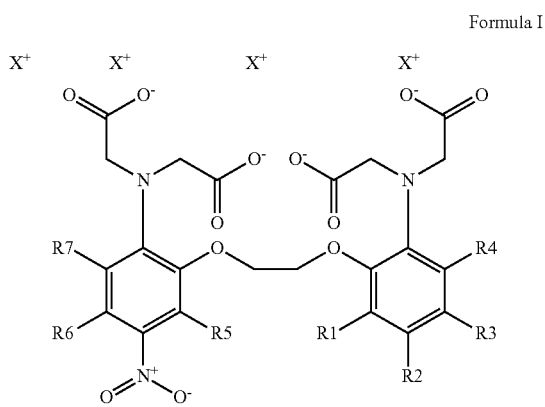

Formula I wherein R1 is selected from hydrogen, halogen, carboxy, alkyl and formyl, R2 is independently selected from hydrogen, halogen, alkyl, alkoxy, morpholino, CN, carboxy and formyl, R3 is independently selected from hydrogen, halogen, N-alkyl sulfate, carboxy, alkoxy, phenyl, CN, CF3, and tertiary butyl, R4 is independently selected from hydrogen, halogen or alkyl, R5 and R7 independently are hydrogen or alkyl R6 is selected from hydrogen, alkyl, alkoxy and halogen, or wherein R3 and R4 form an aromatic bridge and X+ is a positively charged counter ion, thereby binding calcium ions to the compound b) releasing calcium ions from the compound, wherein said release causes a change in absorbance of the compound c) measuring the change in absorbance d) using the change in absorbance measured in (c) for determining the concentration of calcium ions.

2. The method according to 1, wherein the solution comprising the compound of Formula I has a pH in the range from pH 8.5 to pH 11.5.

3. The method according to 1 or 2, wherein the solution comprising the compound of Formula I has a pH in the range from pH 9.0 to pH 10.5.

4. The method according to any of 1 to 3, wherein R1 of Formula I is either hydrogen or halogen.

5. The method according to any of 1 to 3, wherein R2 of Formula I is hydrogen, halogen or alkyl.

6. The method according to any of 1 to 3, wherein R3 of Formula I is hydrogen, halogen, carboxy or alkoxy.

7. The method according to any of 1 to 3, wherein the release of calcium ions in step (b) of 1 is triggered by a calcium chelating agent having at 20° C. a binding constant for calcium ions of log k equal to 7.0 or above.

8. The method according to 7, wherein the release of calcium ions in step (b) of 1 is triggered by EDTA, DTPA, EGTA, DTPMP and/or EDPMP.

9. A reagent for measurement of calcium having a pH ranging from pH 8.5 to pH 11.5, containing a compound of Formula I as defined in 1.

10. The reagent of 9, comprising the compound of Formula I in a concentration ranging from 0.10 mM to 50 mM.

11. The reagent of 9, wherein comprising a buffer system, wherein the buffer system is selected from AMPD (=2-Amino-2-Methyl-1,3-propanediol), CHES (=2-(N-Cyclohexylamino)-ethanesulfonic acid), AMPSO (=3-[Dimethyl(hydroxylmethyl)-methylamino]-2-hydroxypropane-sulfonic acid), CAPSO (=3-Cyclohexylamino)-2-hydroxy-1-propanesulfonic acid), CAPS (=3-Cyclohexylamino)-2-propanesulfonic acid), a glycine buffer system or a carbonate buffer system.

12. The reagent according to any of 9 to 11, wherein R1 of Formula I is either hydrogen or halogen.

13. The reagent according to any of 9 to 11, wherein R2 of Formula I is hydrogen, halogen or alkyl.

14. The reagent according to any of 9 to 11, wherein R3 of Formula I is hydrogen, halogen, carboxy or alkoxy.

15. A test kit for the measurement of calcium, the test kit comprising the reagent according to any of 9 to 14.

EXAMPLES

Example 1

Synthesis of NM-BAPTA

The synthesis of NM-BAPTA is schematically depicted in FIG. 1.

a) 1-(2-Chloro-ethoxy)-2-nitro-benzene

2-Nitro-phenol (168.7 g) and toluene-4-sulfonic acid 2-chloroethyl ester (100 g) were dissolved in 500 ml DMF and were stirred for 1 h at 110-120° C. after careful addition of 199 g potassium carbonate. The reaction mixture was poured in a mixture of crushed ice and water (8 L) which was vigorously stirred. The residue was filtered off, washed several times with water and dried. Yield: 100-120 g.

b) 4-Methyl-1-nitro-2-(2-(2-nitro-phenoxy)-ethoxy)-benzene 1-(2-Chloro-ethoxy)-2-nitro-benzene (116 g) and 5-methyl-2-nitro-phenol (88 g) were dissolved in 500 ml DMF and was stirred for 4 h at 90-110° C. after careful addition of 160 g potassium carbonate. The reaction mixture was poured in a mixture of crushed ice and water (8 l) which was vigorously stirred. The residue was filtered off, washed several times with water and dried. The crude product was suspended in methanol and the pale yellow residue was again filtered off, washed with methanol and dried. Yield: 150-165 g.

c) 2-(2-(2-Amino-phenoxy)-ethoxy)-4-methyl-phenylamine 100 g 4-methyl-1-nitro-2-(2-(2-nitro-phenoxy)-ethoxy)-benzene and 10 g palladium on charcoal were suspended in 3.5 l dioxane and hydrogenated at room temperature under a hydrogen pressure of 5.5 bar. After flashing three times with nitrogen the catalyst was filtered off under a nitrogen atmosphere and the remaining solution was evaporated and the product was dried under vacuum. Yield: 80 g.

d) ((2-(2-(2-(Bis-methoxycarbonylmethyl-amino)-phenoxy)-ethoxy)-4-methyl-phenyl)-methoxycabonylmethyl-amino)-acetic acid methyl ester 2-(2-(2-Amino-phenoxy)-ethoxy)-4-methyl-phenylamine (80 g) were dissolved in 2.5 l DMF and 285 ml bromo-acetic acid methyl ester, 429 g potassium carbonate, and 36.8 g sodium iodide were added. The reaction mixture was heated up to 80° C. for 2 h. After evaporation the remaining bromo-acetic acid methyl ester was removed from the product with hexane. The crude product was further purified by crystallization in methanol. Yield: 93 g.

e) ((2-(2-(2-(Bis-methoxycarbonylmethyl-amino)-5-nitro-phenoxy)-ethoxy)-4-methyl-phenyl)-methoxycabonylmethyl-amino)-acetic acid methyl ester 50 g ((2-(2-(2-(Bis-methoxycarbonylmethyl-amino)-phenoxy)-ethoxy)-4-methyl-phenyl)-methoxycabonylmethyl-amino)-acetic acid methyl ester were dissolved in 600 ml glacial acetic acid. Under vigorous stirring 91.5 ml 1 molar nitric acid in glacial acetic acid was added and in a second step 28 ml of concentrated sulfuric acid was added. The temperature increased up to 30° C. The reaction mixture was directly poured in a 10 l ice/water mixture. The residue was filtered off, washed several times with water and dried under vacuum. The crude product was further purified by column chromatography on silica gel first with hexane/acetic acid ethyl ester (1:1) as eluent and a second time with toluene/acetonitrile (1:1) as eluent. The product was finally crystallized from propan-2-ol. Yield: 20 g.

f) NM-BAPTA; Potassium salt of ((2-(2-(2-(bis-carboxymethyl-amino)-5-nitro-phenoxyl)-ethoxy)-4-methyl-phenyl)-carboxymethyl-amino)-acetic acid 9.5 g ((2-(2-(2-(Bis-methoxycarbonylmethyl-amino)-5-nitro-phenoxy)-ethoxy)-4-methyl-phenyl)-methoxycabonylmethyl-amino)-acetic acid methyl ester were dissolved in a mixture of water/methanol (230 ml each) and 160 ml 1 molar potassium hydroxide solution was added. The reaction mixture was refluxed for 1 h. After cooling down to room temperature and adding 250 ml water the solution's pH was adjusted to pH 3 and the methanol was evaporated. The product was isolated by solvent extraction with acidic acid ethyl ester. After evaporation the product was dried under vacuum. The ((2-(2-(2-(bis-carboxymethyl-amino)-5-nitro-phenoxyl)-ethoxy)-4-methyl-phenyl)-carboxymethyl-amino)-acetic acid was dissolved in methanol and the equimolar potassium hydroxide in methanol was added. After evaporation and drying the appropriate potassium salt could be isolated. Yield: 9 g.

Example 2

General Procedure for Measurement of Calcium Ions with NM-BAPTA

The measurement of calcium ions with a mono-nitro-BAPTA-type compound according to Formula I is performed in a back-titration method.

An aliquot of the sample of interest is mixed with a solution comprising the mono-nitro-BAPTA-type compound and incubated. On the automatic analyzers of Roche Diagnostics, Germany, this reagent is called R1. The incubation is performed till a stable base-line signal is obtained. Usually a stable base-line signal is obtained in less than 10 min, mostly within 2 to 5 min.

The mixture of sample and R1 (optionally diluted, e.g. with distilled water) is then analyzed, i.e. the absorbance values at the most appropriate wave-length(s) is(are) or a spectrum is measured.

The calcium ions bound to a compound according to Formula I are then released by addition of a releasing agent, e.g. EDTA. This second reagent is called R2 on the automatic analyzers of Roche Diagnostics, Germany. Where required, the mixture can be further diluted with distilled water.

The final mixture of sample, R1 and R2 (optionally diluted, e.g. with distilled water) is then analyzed, i.e. the absorbance values at the most appropriate wave-length(s) is(are) or a spectrum is measured.

The change in absorbance is directly correlated to the concentration of calcium ions in the sample of interest and the concentration of calcium ions is calculated according to standard procedures.

In Table I an overview is given over the applications recommended for measurement of calcium ions on five different automated analyzers of Roche Diagnostics, Germany. The recommended applications for the Modular P and the Modular D analyzer are identical.

TABLE 1

Recommended pipetting volumes (in μl) for measurement of calcium ions.

|  | HiCo R1 Integra | HiCo R1 cobas | LoCo R1 Roche/Hitachi 902 | LoCo R1 Modular D/ Modular P |
|---|---|---|---|---|
| R1 (reagent 1) | 20 | 20 | 250 | 180 |
| D (distilled water) | 100 | 130 | — | — |
| S (sample) | 3 | 3 | 4 | 3 |
| D (distilled water) | 30 | — | — | — |
| R2 (reagent 2) | 20 | 20 | 28 | 20 |
| D (distilled water) | 50 | 50 | — | — |
| total volume of final mixture | 223 | 223 | 282 | 203 |

HiCo R1 = high concentration R1 reagent;
LoCo R1 = low concentration R1 reagent;
Integra, cobas, Roche/Hitachi 902, Modular D, and Modular P are analyzer systems distributed by Roche Diagnostics, Germany.

TABLE 2

Compositions of HiCo R1, LoCo R1 and R2, respectively

|  | buffer | pH | Brij-35 | NaCl | NM-BAPTA | NaN$_3$ |
|---|---|---|---|---|---|---|
| HiCo-R1 | 557 mmmol/L CAPSO | 10.0 | 0.123% | — | 1.68 mmol/L | 0.09% |
| LoCo-R1 | 57 mmol/L CAPSO | 10.0 | 0.012% | 0.9% | 0.20 mmol/L | 0.09% |
| R2 | 7.5 mmol/L K$_3$-EDTA | 7.3 | 0.012% | 0.9% | — | 0.09% |

Example 3

Linearity of Calcium Measurement Using NM-BAPTA

The method for measurement of calcium ions disclosed in the present disclosure demonstrates a very high precision. This becomes evident if theoretically expected and actually measured values are compared.

Different concentrations of calcium ions (→theoretical values) are compared to values actually measured in the new methods disclosed herein.

Figure 2A:
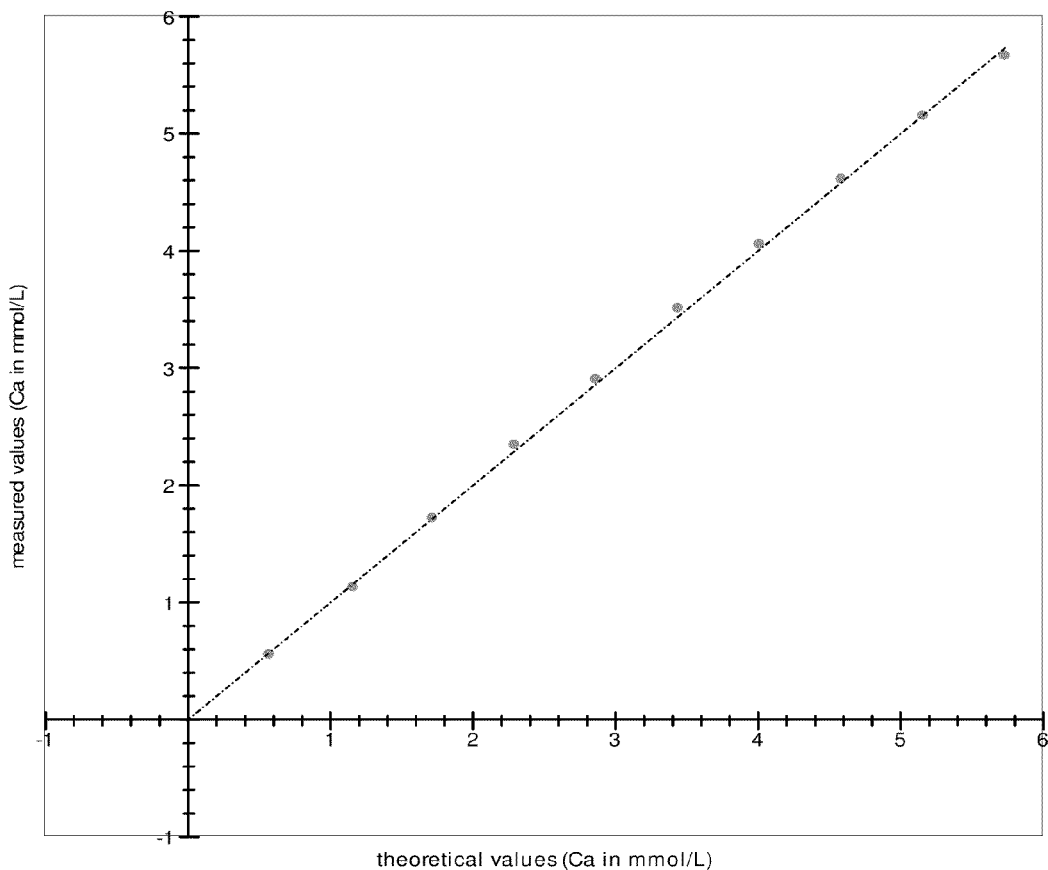
FIG. 2a is a graphical representation of the measurement of calcium ions according to the procedures of Example 2, from a Modular P Analyzer (Roche Diagnostics, Germany) showing the theoretical value and the value actually measured plotted against each other.
Figure 2B:
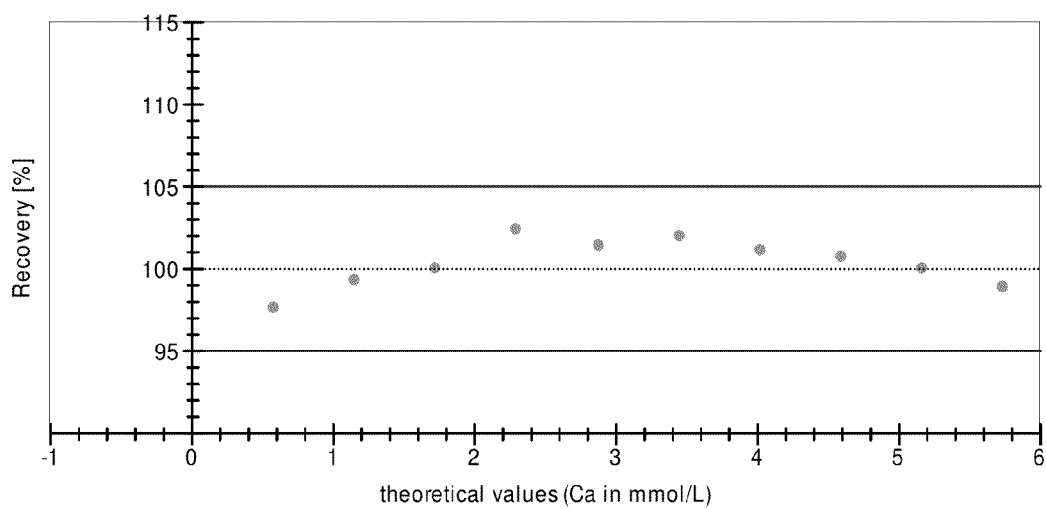
FIG. 2b is a graphical representation of the measurement of calcium ions according to the procedures of Example 2, from a Modular P Analyzer (Roche Diagnostics, Germany) showing the % recovery (e.g., the value actually measured given as a percentage of the expected (theoretical) value).
Figure 3A:
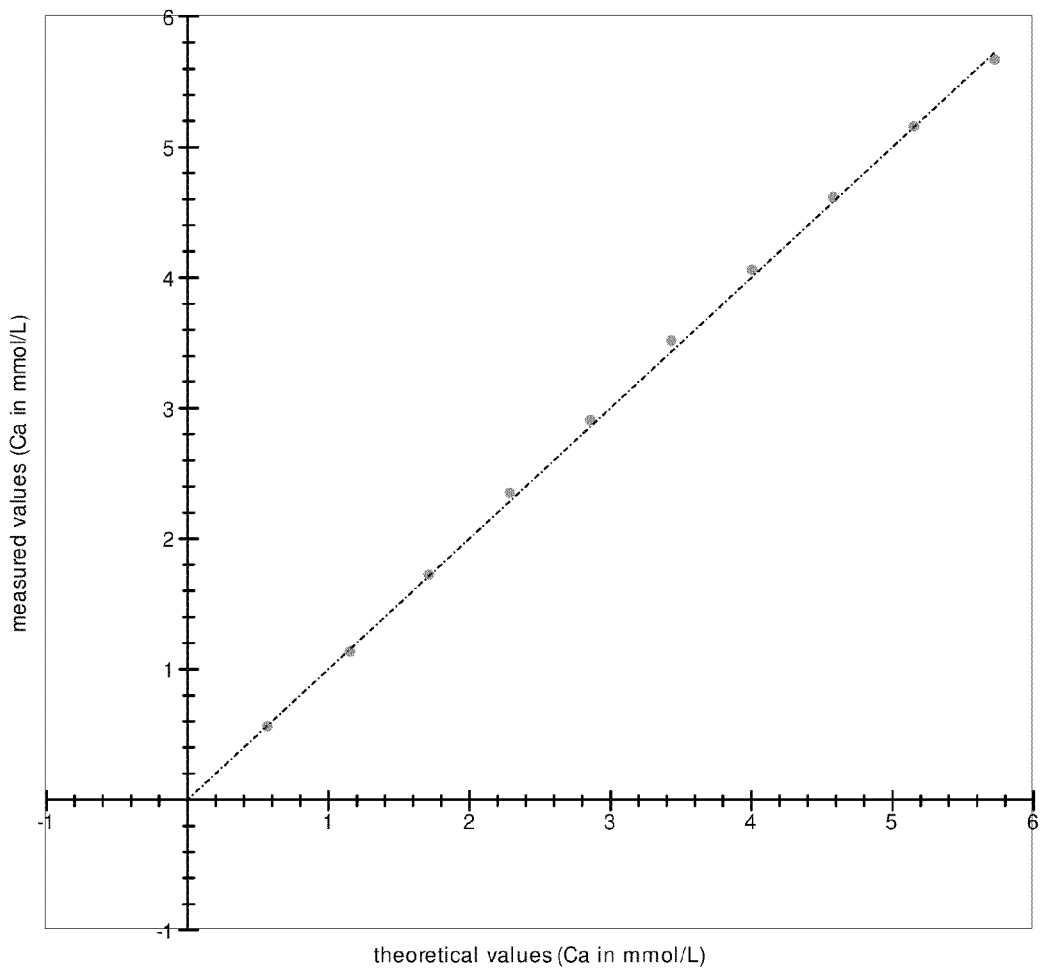
FIG. 3a is a graphical representation of the measurement of calcium ions according to the procedures of Example 2, from the Cobas c501 Analyzer (Roche Diagnostics, Germany) showing the theoretical value and the value actually measured plotted against each other.
Figure 3B:
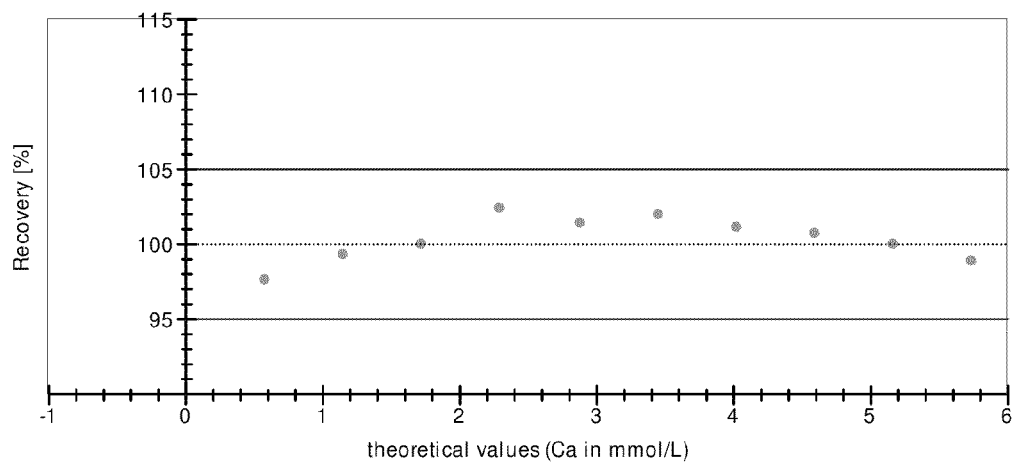
FIG. 3b is a graphical representation of the measurement of calcium ions according to the procedures of Example 2, from the Cobas c501 Analyzer (Roche Diagnostics, Germany) showing the % recovery (e.g., the value actually measured is given as a percentage of the expected (theoretical) value).

Only two representative examples, with values measured on two different analyzers, Modular P and cobas c501 (both distributed by Roche Diagnostics), respectively, are given as FIGS. 2 and 3. These two figures demonstrate the outstanding technical quality/precision of the measurements. As obvious from FIGS. 2 and 3, all values actually measured are within 95 to 105% of the corresponding expected theoretical value, which translates to a rather exact measurement of calcium ions over the whole range of concentrations investigated.

Example 4

Determining the Minimum Concentration of NM-BAPTA

The concentration of calcium ions in the circulation only rarely exceeds 4 mmol/L. A reagent capable of measuring up to 5 mmol/L calcium in a reliable manner should be most appropriate to determine calcium ions in the circulation.

Figure 4A:
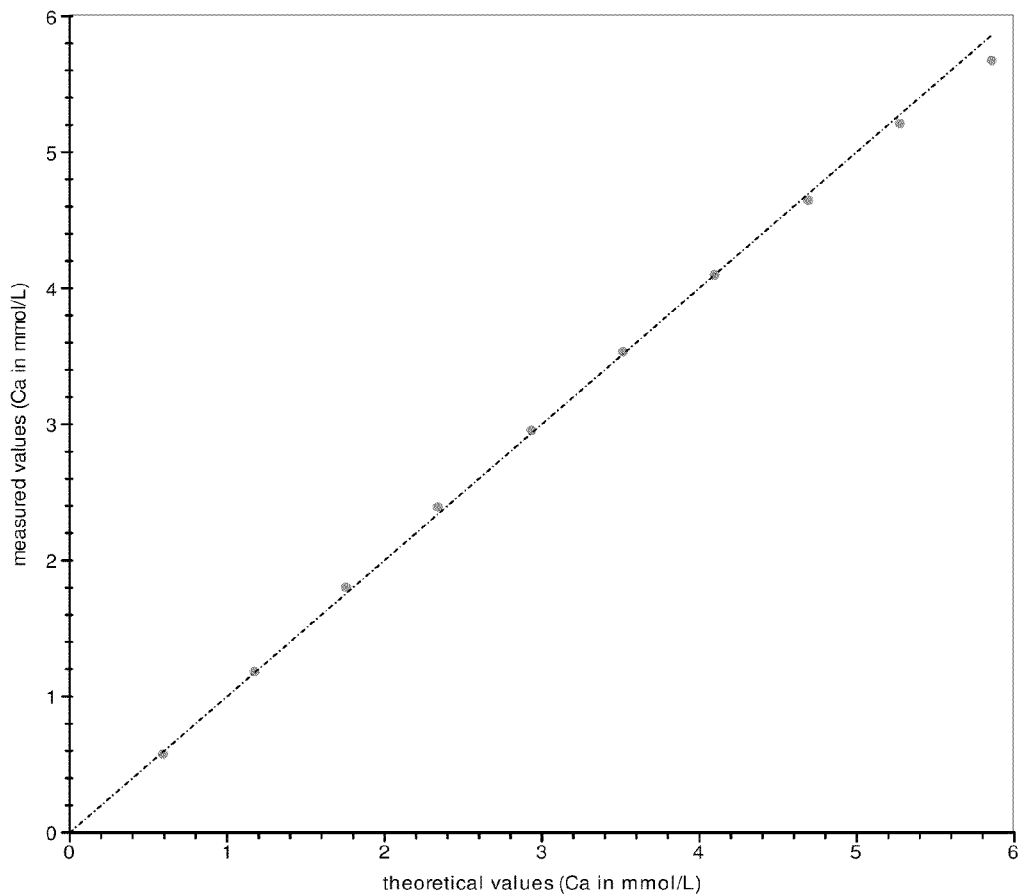
FIG. 4a is a graphical representation of the measurement of calcium ions according to the procedures of Example 2, from the on the Modular P Analyzer (Roche Diagnostics, Germany) where the concentration of NM-BAPTA reduced to 90% of the standard concentration, showing the theoretical value and the value actually measured plotted against each other.
Figure 4B:
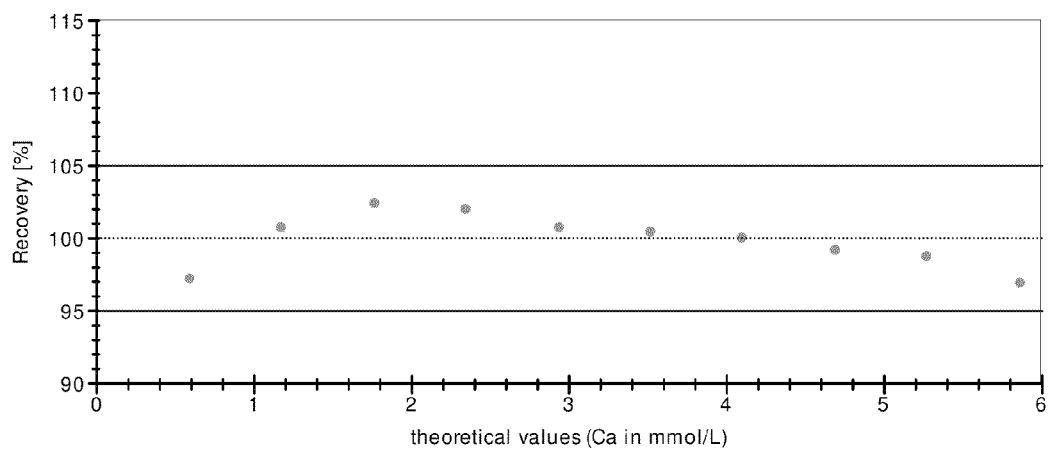
FIG. 4b is a graphical representation of the measurement of calcium ions according to the procedures of Example 2, from the on the Modular P Analyzer (Roche Diagnostics, Germany) where the concentration of NM-BAPTA reduced to 90% of the standard concentration, showing the % recovery (e.g., the value actually measured given as percentage of the expected (theoretical) value).
Figure 5A:
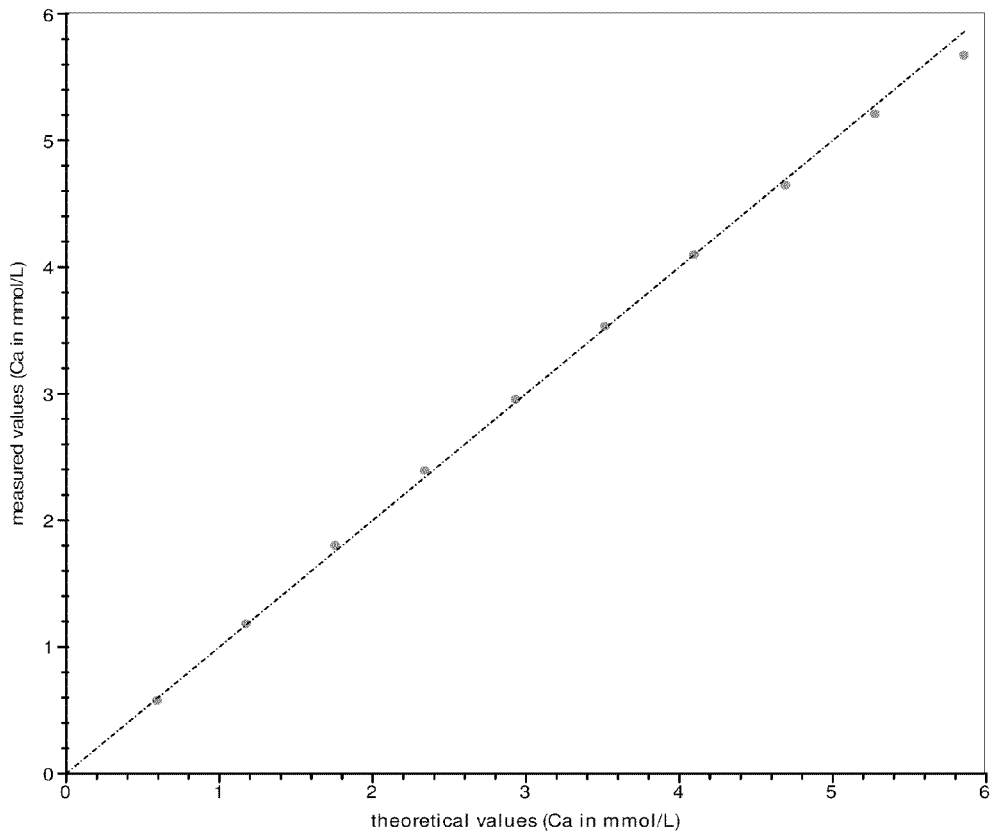
FIG. 5a is a graphical representation of the measurement of calcium ions according to the procedures of Example 2, from the on the Modular P Analyzer (Roche Diagnostics, Germany) where the concentration of NM-BAPTA reduced to 80% of the standard concentration, showing the theoretical value and the value actually measured plotted against each other.
Figure 5B:
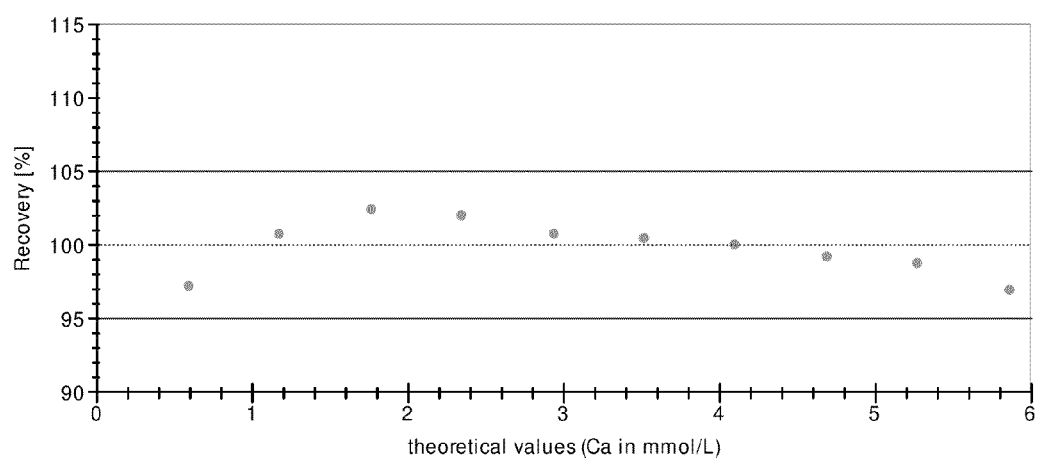
FIG. 5b is a graphical representation of the measurement of calcium ions according to the procedures of Example 2, from the on the Modular P Analyzer (Roche Diagnostics, Germany) where the concentration of NM-BAPTA reduced to 80% of the standard concentration, showing the % recovery (e.g., the value actually measured given as percentage of the expected (theoretical) value).

Various concentrations of calcium ions (expected values in FIGS. 4 and 5) have been measured on the Modular P instrument with the application described in the last column of Table 1. However, only 90% or 80%, respectively, of the regular concentration of NM-BAPTA have been used. As can be seen from FIGS. 4 and 5, respectively, even if only 80% of NM-BAPTA are present in the detection mixture as compared to the standard procedure given in Example 2, calcium ions up to 5 mmol/L are still recovered at between 95 to 105%. As obvious from FIG. 5, values above 5 mM tend to be recovered with too low values if the concentration of NM-BAPTA is reduced to 80%. This means that for measurement of the high concentrations of calcium as present in some pathological samples (in case such sample is diluted about 1:70 as in the above example) the final concentration of NM-BAPTA should be about 0.2 mmol/L in order to secure a correct measurement of calcium ions in those samples.

Example 5 pH-Dependent Stability of NM-BAPTA

A reagent for measurement of calcium should be as stable as possible both under transport conditions as well as on board of an analyzer.

In order to investigate its stability NM-BAPTA has been stored at different pH values. A short term stress model has been applied and the reagent containing NM-BAPTA stored at 35° C. The "stressed" reagent has been used in the measurement of calcium ions under otherwise identical conditions using aliquots of the same samples. The values measured after stressing the reagent have been compared to the values measured with a non-stressed reagent at day zero, i.e. the day when the temperature stress on the reagent was initiated.

The buffer systems used were 100 mmol/L HEPES at pH 7.4, 50 mmol/L Tris at pH 8.0, 50 mmol/L NaHCO3 at pH 10.0, 50 mmol/L Glycin at pH 9.8, and 40 mmol/L CAPSO at pH 10, respectively. The corresponding data are summarized in Tables 3 to 7.

TABLE 3

Stability of NM-BAPTA in 100 mmol/L HEPES pH 7.4 at 35° C.

|  |  | day 0 | day 0 Median | week 1 | week 1 Median | Recovery from day 0 |
|---|---|---|---|---|---|---|
| 0.9% NaCl target | calibrator | 0.11 0.10 0.0 | 0.10 | 0.07 0.17 0.15 | 0.15 |  |
| Calibrator target | calibrator | 0.08 2.55 2.51 2.54 | 2.54 | 1.91 1.94 1.95 | 1.94 | 76.4% |
| PNU lot target | control 176136 2.05 | 2.20 2.07 2.08 | 2.08 | 1.82 1.64 1.69 | 1.69 | 81.3% |
| PPU lot target | control 174531 | 3.08 3.09 3.12 | 3.09 | 2.29 2.27 2.29 | 2.29 | 74.1% |
| Human serum 1 | sample | 2.23 2.24 2.25 | 2.24 | 1.74 1.76 1.76 | 1.76 | 78.6% |
| Human serum 2 | sample | 2.14 2.14 2.12 | 2.14 | 1.66 1.60 1.64 | 1.64 | 76.6% |
| Human plasma 1 | sample | 1.82 1.82 1.82 | 1.82 | 1.47 1.42 1.40 | 1.42 | 78.0% |
| Human plasma 2 | sample | 1.79 1.80 1.84 | 1.80 | 1.42 1.40 1.40 | 1.40 | 77.8% |

As obvious from Table 3, the reagent containing NM-BAPTA is not stable at pH 7.4. The recovery of calcium ions is only in range of 80% or below.

TABLE 4

Stability of NM-BAPTA in 50 mmol/L TRIS pH 8.0 at 35° C.

|  |  | day 0 | day 0 Median | week 1 | week 1 Median | Recovery from day 0 |
|---|---|---|---|---|---|---|
| 0.9% NaCl | calibrator | 0.02 |  | 0.11 |  |  |
|  |  | 0.00 | 0.00 | 0.15 | 0.15 |  |
| target | 0.0 | 0.00 |  | 0.16 |  |  |
| Calibrator | calibrator | 2.49 |  | 2.10 |  |  |
|  |  | 2.48 | 2.49 | 2.13 | 2.12 | 85.1% |
| target | 2.5 | 2.49 |  | 2.12 |  |  |
| PNU control | | 2.04 |  | 1.80 |  |  |
| lot | 176136 | 2.02 | 2.02 | 1.77 | 1.80 | 89.1% |
| target | 2.05 | 2.01 |  | 1.80 |  |  |
| PPU control | | 3.12 |  | 2.47 |  |  |
| lot | 174531 | 3.09 | 3.09 | 2.46 | 2.47 | 79.9% |
| target | 3.32 | 3.07 |  | 2.47 |  |  |
| Human serum 1 | sample | 2.21 |  | 1.97 |  |  |
|  |  | 2.20 | 2.21 | 1.93 | 1.97 | 89.1% |
|  |  | 2.22 |  | 1.97 |  |  |
| Human serum 2 | sample | 2.07 |  | 1.79 |  |  |
|  |  | 2.08 | 2.08 | 1.81 | 1.81 | 87.0% |
|  |  | 2.08 |  | 1.84 |  |  |
| Human plasma 1 | sample | 1.80 |  | 1.55 |  |  |
|  |  | 1.80 | 1.80 | 1.55 | 1.55 | 86.1% |
|  |  | 1.77 |  | 1.55 |  |  |
| Human plasma 2 | sample | 1.77 |  | 1.54 |  |  |
|  |  | 1.77 | 1.77 | 1.54 | 1.54 | 87.0% |
|  |  | 1.78 |  | 1.54 |  |  |

As obvious from Table 4, the reagent containing NM-BAPTA has a borderline, but still acceptable stability at pH 8.0. The recovery of calcium ions is mostly in the range of 80% to 90%.

TABLE 5

Stability of NM-BAPTA in 50 mmol/L NaHCO3 pH 10.0 at 35° C.

|  |  | day 0 | day 0 Median | week 1 | week 1 Median | Recovery from day 0 |
|---|---|---|---|---|---|---|
| 0.9% NaCl | calibrator | 0.04 |  | 0.13 |  |  |
|  |  | 0.01 | 0.01 | 0.13 | 0.13 |  |
| target | 0.0 | 0.01 |  | 0.11 |  |  |
| Calibrator | calibrator | 2.48 |  | 2.53 |  |  |
|  |  | 2.48 | 2.48 | 2.57 | 2.57 | 103.6% |
| target | 2.5 | 2.46 |  | 2.59 |  |  |
| PNU control | | 2.04 |  | 2.04 |  |  |
| lot | 176136 | 1.98 | 1.98 | 2.04 | 2.04 | 103.0% |
| target | 2.05 | 1.98 |  | 2.03 |  |  |
| PPU control | | 3.10 |  | 3.16 |  |  |
| lot | 174531 | 3.08 | 3.08 | 3.20 | 3.17 | 102.9% |
| target | 3.32 | 3.07 |  | 3.17 |  |  |
| Human serum 1 | sample | 2.18 |  | 2.21 |  |  |
|  |  | 2.21 | 2.18 | 2.26 | 2.24 | 102.8% |
|  |  | 2.18 |  | 2.24 |  |  |
| Human serum 2 | sample | 2.02 |  | 2.10 |  |  |
|  |  | 2.05 | 2.05 | 2.11 | 2.11 | 102.9% |
|  |  | 2.05 |  | 2.19 |  |  |
| Human plasma 1 | sample | 1.75 |  | 1.88 |  |  |
|  |  | 1.76 | 1.76 | 1.80 | 1.81 | 102.8% |
|  |  | 1.76 |  | 1.81 |  |  |
| Human plasma 2 | sample | 1.73 |  | 1.78 |  |  |
|  |  | 1.74 | 1.74 | 1.81 | 1.80 | 103.4% |
|  |  | 1.75 |  | 1.80 |  |  |

TABLE 6

Stability of NM-BAPTA in 50 mmol/L Glycin pH 9.8 at 35° C.

|  |  | day 0 | day 0 Median | week 1 | week 1 Median | Recovery from day 0 |
|---|---|---|---|---|---|---|
| 0.9% NACL | calibrator | −0.03 |  | −0.03 |  |  |
|  |  | −0.05 | −0.05 | −0.05 | −0.03 |  |
| target | 0.0 | −0.05 |  | −0.03 |  |  |
| CACO3 | calibrator | 2.48 |  | 2.49 |  |  |
|  |  | 2.52 | 2.48 | 2.45 | 2.46 | 99.2% |
| target | 2.5 | 2.47 |  | 2.46 |  |  |
| PNU control | | 2.07 |  | 2.05 |  |  |
| lot | 176136 | 2.07 | 2.07 | 2.08 | 2.05 | 99.0% |
| target | 2.05 | 2.01 |  | 2.02 |  |  |
| PPU control | | 3.11 |  | 3.07 |  |  |
| lot | 174531 | 3.09 | 3.09 | 3.12 | 3.12 | 101.0% |
| target | 3.32 | 3.04 |  | 3.12 |  |  |
| Human serum 1 | sample | 2.26 |  | 2.22 |  |  |
|  |  | 2.29 | 2.26 | 2.23 | 2.23 | 98.7% |
|  |  | 2.26 |  | 2.23 |  |  |
| Human serum 2 | sample | 2.34 |  | 2.24 |  |  |
|  |  | 2.32 | 2.34 | 2.25 | 2.25 | 96.2% |
|  |  | 2.34 |  | 2.28 |  |  |
| Human plasma 1 | sample | 1.91 |  | 1.75 |  |  |
|  |  | 1.88 | 1.89 | 1.73 | 1.73 | 91.5% |
|  |  | 1.89 |  | 1.73 |  |  |
| Human plasma 2 | sample | 1.92 |  | 1.69 |  |  |
|  |  | 1.76 | 1.76 | 1.72 | 1.71 | 97.2% |
|  |  | 1.75 |  | 1.71 |  |  |

TABLE 7

Stability of NM-BAPTA in 40 mmol/L CAPSO, pH 10.0 at 35° C.

|  |  | day 0 | day 0 median | day 7 | day 7 median | Recovery from day 0 |
|---|---|---|---|---|---|---|
| 0.9% NaCl | calibrator | −0.02 |  | −0.08 |  |  |
|  |  | −0.01 | −0.02 | −0.11 | −0.09 |  |
| target | 0.0 | −0.04 |  | −0.09 |  |  |
| Calibrator | calibrator | 2.50 |  | 2.47 |  |  |
|  |  | 2.58 | 2.57 | 2.47 | 2.47 | 95.9% |
| Sollwert | 2.5 | 2.57 |  | 2.42 |  |  |
| PNU control | | 2.21 |  | 2.14 |  |  |
| lot | 179596 | 2.17 | 2.19 | 2.12 | 2.12 | 96.6% |
| target | 2.12 | 2.19 |  | 2.08 |  |  |
| PPU control | | 3.39 |  | 3.28 |  |  |
| lot | 176287 | 3.35 | 3.35 | 3.30 | 3.29 | 98.2% |
| target | 3.26 | 3.31 |  | 3.29 |  |  |
| Human serum 1 | Probe | 2.09 |  | 1.99 |  |  |
|  |  | 2.12 | 2.09 | 2.07 | 2.02 | 96.7% |
|  |  | 2.06 |  | 2.02 |  |  |
| Human serum 2 | Probe | 2.20 |  | 2.16 |  |  |
|  |  | 2.20 | 2.20 | 2.11 | 2.16 | 98.4% |
|  |  | 2.21 |  | 2.20 |  |  |
| Human plasma 1 | Probe | 2.04 |  | 2.07 |  |  |
|  |  | 2.06 | 2.06 | 2.03 | 2.03 | 98.4% |
|  |  | 2.08 |  | 1.97 |  |  |
| Human plasma 2 | Probe | 2.12 |  | 2.06 |  |  |
|  |  | 2.05 | 2.11 | 2.06 | 2.06 | 97.8% |
|  |  | 2.11 |  | 2.09 |  |  |

As obvious from Tables 5 to 7 the reagent disclosed in the present application has an excellent stability at a pH around 10. The recovery of calcium ions after stressing such reagent at 35° C. for one week is excellent and by large in the desired range of between 90% to 110%, mostly even between 95% and 105%. This high stability can be achieved irrespective of the buffer system used.

Example 6

No Interference by Magnesium in Calcium Measurements Using NM-BAPTA

A sample comprising calcium ions in a physiological concentration of 2.53 mmol/L has been spiked with 0 to 15 mmol/L magnesium ions. The spiked samples were measured on a Roche/Hitachi 917 analyzer in an application as given in Example 2 for Modular P. Median results of triple determinations are given in Table 8 below.

TABLE 8

No effect on calcium ion measurements by magnesium ions.

| Magnesium (mmol/L) | Calcium measured (mmol/L) | recovery (%) |
|---|---|---|
| 0.0 | 2.53 | 100.0 |
| 1.5 | 2.52 | 99.6 |
| 3.0 | 2.52 | 99.6 |
| 4.5 | 2.55 | 100.8 |
| 6.0 | 2.55 | 100.8 |
| 7.5 | 2.55 | 100.8 |
| 9.0 | 2.55 | 100.8 |
| 10.5 | 2.55 | 100.8 |
| 12.0 | 2.54 | 100.4 |
| 13.5 | 2.54 | 100.4 |
| 15.0 | 2.54 | 100.4 |

As obvious from the recovery values given in Table 8, in the above experiment magnesium ions do not interfere with the measurement of calcium ions.

Example 7

No Interference by Gadolinium in Calcium Measurements Using NM-BAPTA

One sample comprising calcium ions in a physiological concentration of about 2.35 mmol/L as well one sample with elevated level of calcium ions of about 3.40 mmol/L have been spiked with different levels of Omniscan® (C1: 14 µL ad 986 µL, C2: 2.8 µL ad 997 µL). Omniscan® is a frequently used contrast agent comprising gadolinium. The spiked samples have been measured on a Hitachi 917 analyzer in an application as given in Example 2 for Modular P. Median results of triple determination are given in Table 9 below.

TABLE 9

No effect on calcium ion measurements by gadolinium ions.

| | Calcium measured (mmol/L) | Median (mmol/L) | recovery of value without gadolinium (%) |
|---|---|---|---|
| C1_NORMAL plus gadolinium | 2.35<br>2.37<br>2.37 | 2.37 | 101.3 |
| C1_REF_NORMAL (no gadolinium) | 2.32<br>2.34<br>2.34 | 2.34 | |
| C2_NORMAL plus gadolinium | 2.33<br>2.37<br>2.37 | 2.37 | 100.4 |
| C2_REF_NORMAL (no gadolinium) | 2.36<br>2.35<br>2.37 | 2.36 | |
| C1_HIGH plus gadolinium | 3.42<br>3.40<br>3.40 | 3.40 | 100.3 |
| C1_REF_HIGH (no gadolinium) | 3.39<br>3.39<br>3.33 | 3.39 | |
| C2_HIGH plus gadolinium | 3.43<br>3.44<br>3.40 | 3.43 | 100.6 |
| C2_REF_HIGH (no gadolinium) | 3.41<br>3.40<br>3.41 | 3.41 | |

As obvious from the recovery values given in Table 9, in the above experiment gadolinium ions do not interfere with the measurement of calcium ions, because all values measured are well with the 95 to 105% recovery range.

Example 8

Synthesis of NF-BAPTA

Figure 6:
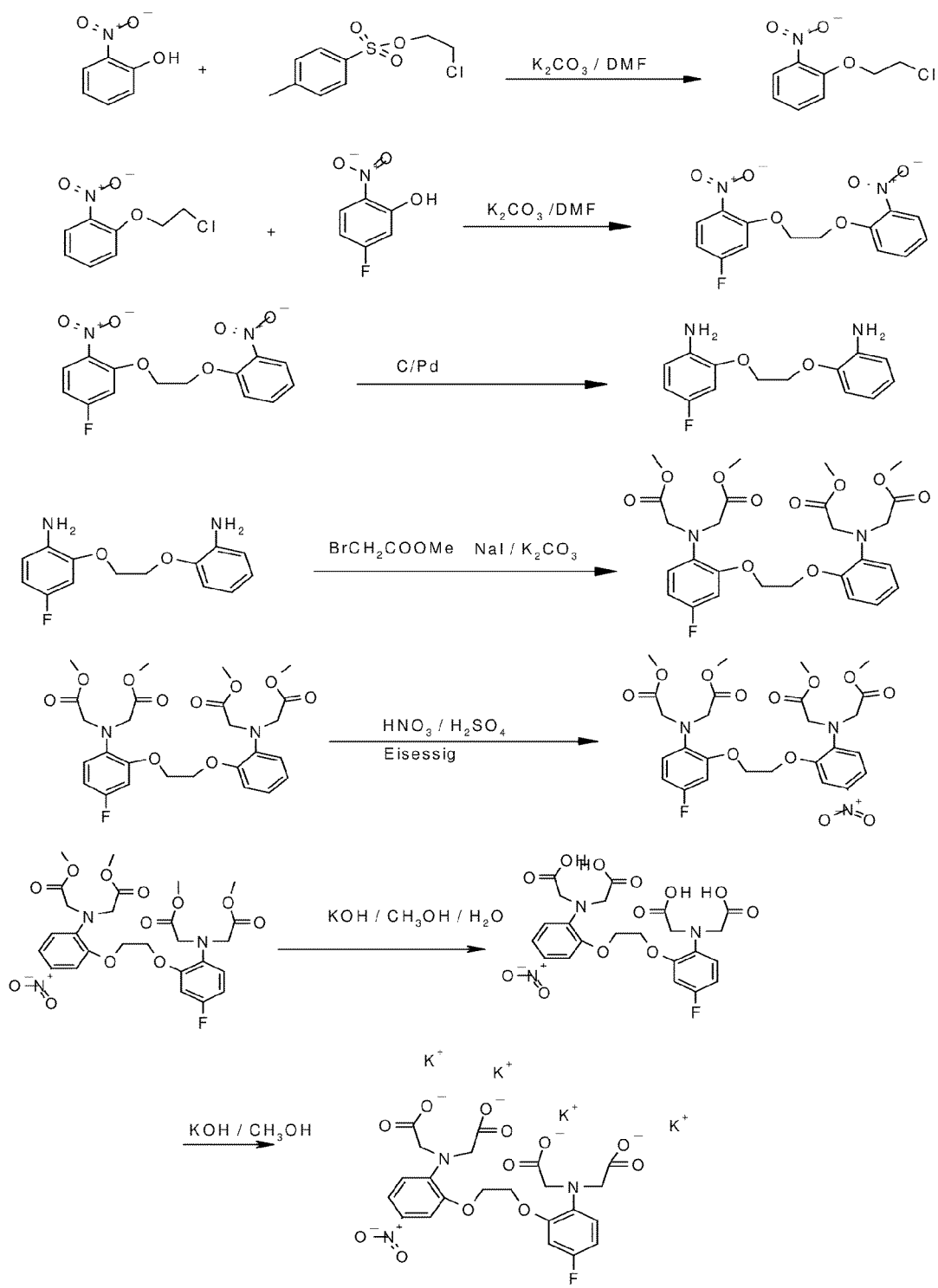
FIG. 6 is a schematic depiction of synthesis of NF-BAPTA.

The synthesis of NF-BAPTA is schematically depicted in FIG. 6.

a) 1-(2-Chloro-ethoxy)-2-nitro-benzene (See Example 1).

b) 4-Fluoro-1-nitro-2-(2-(2-nitro-phenoxy)-ethoxy)-benzene 1-(2-Chloro-ethoxy)-2-nitro-benzene (10 g) and 5-fluoro-2-nitro-phenol (7.86 g) were dissolved in 50 ml DMF and was stirred for 19 h at 90-110° C. after careful addition of 13.82 g potassium carbonate. The reaction mixture was poured in a mixture of crushed ice and water (500 ml) which was vigorously stirred. The residue was filtered off, washed several times with water and dried. The crude product was suspended in methanol and the pale yellow residue was again filtered off, washed with methanol and dried. Yield: 9.5 g.

c) 2-(2-(2-Amino-phenoxy)-ethoxy)-4-fluoro-phenylamine 9.48 g 4-fluoro-1-nitro-2-(2-(2-nitro-phenoxy)-ethoxy)-benzene and 1.5 g palladium on charcoal were suspended in 500 ml dioxane and 60 ml glacial acetic acid and hydrogenated at room temperature. After flashing three times with nitrogen the catalyst was filtered off under a nitrogen atmosphere and the remaining solution was evaporated and the product was dried under vacuum. Yield: 7.52 g.

d) ((2-(2-(2-(Bis-methoxycarbonylmethyl-amino)-phenoxy)-ethoxy)-4-fluoro-phenyl)-methoxycabonylmethyl-amino)-acetic acid methyl ester 2-(2-(2-Amino-phenoxy)-ethoxy)-4-fluoro-phenylamine (7.52 g) were dissolved in 250 ml DMF and 38.4 ml bromo-acetic acid methyl ester, 56 g potassium carbonate, and 2.13 g sodium iodide were added. The reaction mixture was heated up to 80° C. for 21 h. After evaporation the remaining bromo-acetic acid methyl ester was removed from the product with hexane. The crude product was further purified by crystallization in methanol. Yield: 4.14 g.

e) ((2-(2-(2-(Bis-methoxycarbonylmethyl-amino)-5-nitro-phenoxy)-ethoxy)-4-fluoro-phenyl)-methoxy-cabonylmethyl-amino)-acetic acid methyl ester 2.5 g ((2-(2-(2-(Bis-methoxycarbonylmethyl-amino)-phenoxy)-ethoxy)-4-fluoro-phenyl)-methoxycabonylmethyl-amino)-acetic acid methyl ester were dissolved in 30 ml glacial acetic acid. Under vigorous stirring 4.54 ml 1 molar nitric acid in glacial acetic acid was added and in a second step 11.35 ml of concentrated sulfuric acid was added. The temperature increased up to 30° C. The reaction mixture was directly poured in a 250 ml ice/water mixture. The residue was filtered off, washed several times with water and dried under vacuum. The crude product was further purified by column chromatography on silica gel first with hexane/acetic acid ethyl ester (1:1) as eluent and a second time with toluene/acetonitrile (1:1) as eluent. Yield: 0.82 g.

f) NM-BAPTA; Potassium salt of ((2-(2-(2-(bis-carboxymethyl-amino)-5-nitro-phenoxyl)-ethoxy)-4-fluoro-phenyl)-carboxymethyl-amino)-acetic acid 0.82 g ((2-(2-(2-(Bis-methoxycarbonylmethyl-amino)-5-nitro-phenoxy)-ethoxy)-4-mfluoro-phenyl)-methoxycabonylmethyl-amino)-acetic acid methyl ester were dissolved in a mixture of water/methanol (20 ml each) and 13.77 ml 1 molar potassium hydroxide solution was added. The reaction mixture was refluxed for 1 h. After cooling down to room temperature and adding 250 ml water the solution's pH was adjusted to pH 3 and the methanol was evaporated. The product was isolated by solvent extraction with acidic acid ethyl ester. After evaporation the product was dried under vacuum.

The ((2-(2-(2-(bis-carboxymethyl-amino)-5-nitro-phenoxyl)-ethoxy)-4-fluoro-phenyl)-carboxymethyl-amino)-acetic acid was dissolved in methanol and the equimolar potassium hydroxide in methanol was added. After evaporation and drying the appropriate potassium salt could be isolated. Yield: 0.75 g.

Example 9

Binding of Calcium Ions to NF-BAPTA

The absorbance characteristics of NF-BAPTA in the presence and absence of calcium ions were analyzed using an Uvikon 930 photometer. Absorbance spectra were taken with 0.15 mmol/L NM-BAPTA or NF-BAPTA, respectively, in 50 mmol/L CAPSO (at pH 7), 0.9% NaCl and 0.01% Brij-35 either in the absence or in the presence of 0.09 mmol/L Ca2+, respectively.

Figure 7:
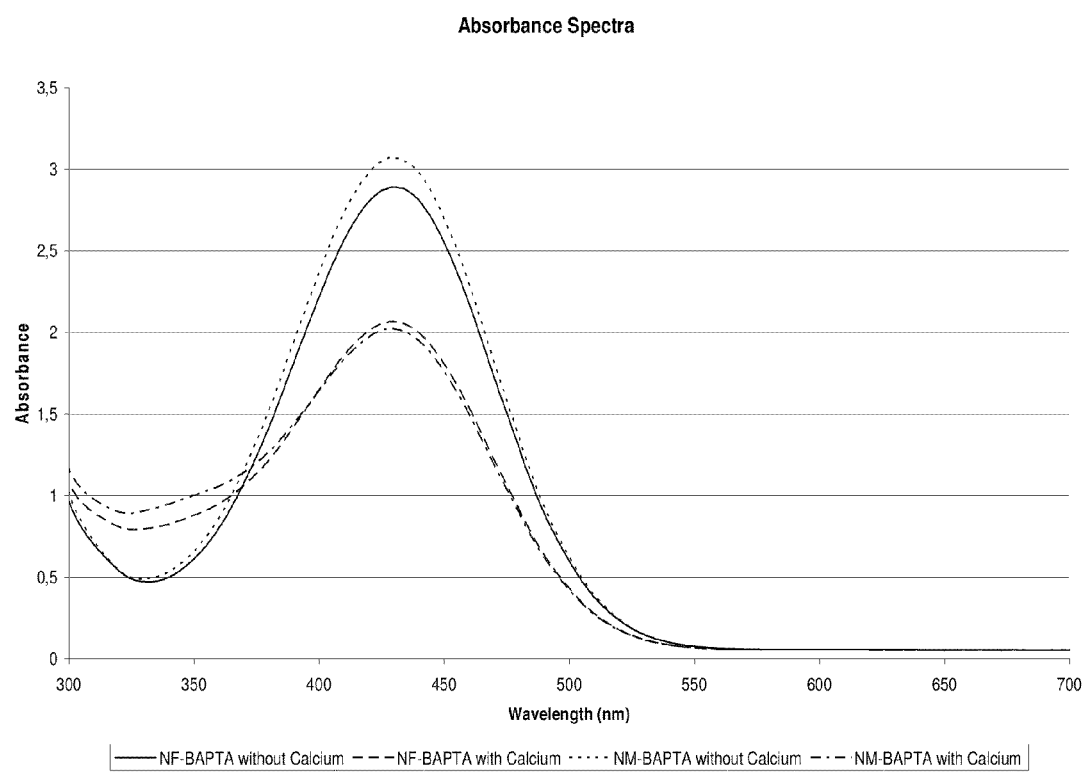
FIG. 7 is an absorbance spectra for NM-BAPTA and NF-BAPTA, respectively, both in the presence and absence of calcium ions, respectively.

As shown in FIG. 7, the absorbance spectra for NM-BAPTA or NF-BAPTA, respectively, are very much alike, indicating that both these compounds, i.e. compounds according to Formula I in general, can be used in the measurement of calcium ions.

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method of measuring calcium ion concentration in a sample, the method comprising the steps of
a) mixing a sample with a solution thereby forming a mixture, the solution having a pH in a range of from 9.0 to 10.5 and comprising a compound having a chemical structure represented by Formula I:

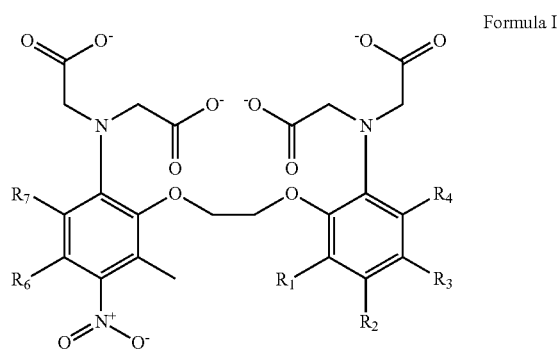

Formula I wherein $R_1$ is selected from the group consisting of hydrogen, halogen, carboxy, alkyl and formyl; $R_2$ is independently selected from the group consisting of hydrogen, halogen, alkyl, alkoxy, morpholino, CN, carboxy and formyl; $R_3$ is independently selected from the group consisting of hydrogen, halogen, N-alkyl sulfate, carboxy, alkoxy, phenyl, CN, $CF_3$, and tertiary butyl; $R_4$ is independently selected from the group consisting of hydrogen, halogen or alkyl; $R_5$ and $R_7$ are independently selected from the group consisting of hydrogen or alkyl; $R_6$ is selected from group consisting of hydrogen, alkyl, alkoxy and halogen; or wherein $R_3$ and $R_4$ form an aromatic bridge and the solution further comprising a positively charged counter ion,
b) incubating the mixture for a period of time, whereby calcium ions within the sample bind to the compound;
c) measuring a baseline absorbance value of the mixture;
d) adding a releasing agent to the mixture;
e) incubating the mixture of the sample, the solution, and the releasing agent for a period of time, whereby calcium ions release from the compound;
f) measuring a second absorbance value of the mixture of the sample, the solution, and the releasing agent;
g) calculating a difference in the baseline absorbance value and the second absorbance value; and
h) determining a concentration of calcium ions within the sample based on said step of calculating.

2. The method according to claim 1, wherein $R_1$ of Formula I is selected from the group consisting of hydrogen and halogen.

3. The method according to claim 1, wherein $R_2$ of Formula I is selected from the group consisting of hydrogen, halogen and alkyl.

4. The method according to claim 1, wherein $R_3$ of Formula I is selected from the group consisting of hydrogen, halogen, carboxy and alkoxy.

5. The method of claim 1 wherein the solution has a pH in the range of from 9.8 to 10.0.

6. The method according to claim 1, wherein the releasing agent is a calcium chelating agent having a binding constant for calcium ions of log k of at least 7.0 at 20° C.

7. The method according to claim 6, wherein the releasing agent is selected from the group consisting of EDTA, DTPA, EGTA, DTPMP and EDPMP.

8. A reagent for measuring calcium ion concentration in a sample, the reagent comprising an aqueous solution having a pH in a range of from 9.0 to 10.5, a positively charged counter ion, and a compound having a chemical structure represented by Formula I:

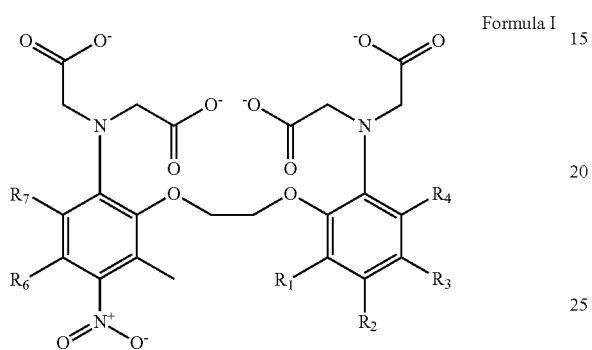

wherein $R_1$ is selected from the group consisting of hydrogen, halogen, carboxy, alkyl and formyl; $R_2$ is independently selected from the group consisting of hydrogen, halogen, alkyl, alkoxy, morpholino, CN, carboxy and formyl; $R_3$ is independently selected from the group consisting of hydrogen, halogen, N-alkyl sulfate, carboxy, alkoxy, phenyl, CN, $CF_3$, and tertiary butyl; $R_4$ is independently selected from the group consisting of hydrogen, halogen or alkyl; $R_5$ and $R_7$ are independently selected from the group consisting of hydrogen or alkyl; $R_6$ is selected from group consisting of hydrogen, alkyl, alkoxy and halogen; or wherein $R_3$ and $R_4$ form an aromatic bridge.

9. The reagent of claim 8 comprising the compound in a concentration ranging from 0.10 mM to 2.0 mM.

10. The reagent of claim 8 comprising a buffer system, wherein the buffer system is selected from the group consisting of (2-Amino-2-Methyl-1,3-propanediol), (2-(N-Cyclohexylamino)-ethanesulfonic acid), (3-[Dimethyl(hydroxylmethyl0-methylamino]-2-hydroxypropane-sulfonic acid), (3-Cyclohexylamino)-2-hydroxy-1-propanesulfonic acid), (3-Cyclohexylamino)-2-propanesulfonic acid), a glycine buffer system, and a carbonate buffer system.

11. The reagent according to claim 8, wherein $R_1$ of Formula I is selected from the group consisting of hydrogen and halogen.

12. The reagent according to claim 8, wherein $R_2$ of Formula I is selected from the group consisting of hydrogen, halogen and alkyl.

13. The reagent according to claim 8, wherein $R_3$ of Formula I is selected from the group consisting of hydrogen, halogen, carboxy, and alkoxy.

14. A kit for measuring calcium ion concentration in a sample, the kit comprising:
 a reagent comprising an aqueous solution having a pH in a range of from 9.0 to 10.5, a positively charged counter ion, and a compound having a chemical structure represented by Formula I

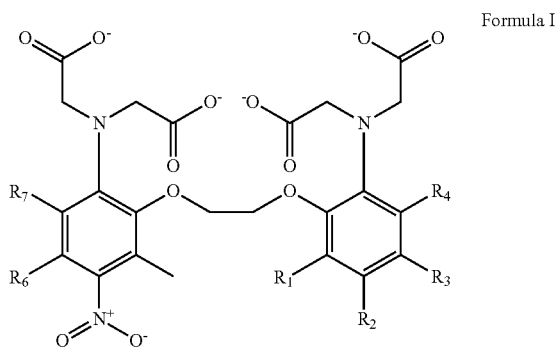

wherein $R_1$ is selected from the group consisting of hydrogen, halogen, carboxy, alkyl and formyl; $R_2$ is independently selected from the group consisting of hydrogen, halogen, alkyl, alkoxy, morpholino, CN, carboxy and formyl; $R_3$ is independently selected from the group consisting of hydrogen, halogen, N-alkyl sulfate, carboxy, alkoxy, phenyl, CN, $CF_3$, and tertiary butyl; $R_4$ is independently selected from the group consisting of hydrogen, halogen or alkyl; $R_5$ and $R_7$ are independently selected from the group consisting of hydrogen or alkyl; $R_6$ is selected from group consisting of hydrogen, alkyl, alkoxy and halogen; or wherein $R_3$ and $R_4$ form an aromatic bridge; and
 a releasing agent, the releasing agent having a binding constant for calcium ions of log k of at least 7.0 at 20° C.

15. The kit of claim 14 wherein the reagent comprising the compound has a concentration ranging from 0.10 mM to 2.0 mM.

16. The kit of claim 14, wherein the aqueous solution further comprises one of the group consisting of (2-Amino-2-Methyl-1,3-propanediol), (2-NCyclohexylamino)-ethanesulfonic acid), (3-[Dimethyl(hydroxylmethyl)methylamino]-2-hydroxypropane-sulfonic acid), (3-Cyclohexylamino)-2-hydroxy-1-propanesulfonic acid), (3-Cyclohexylamino)-2-propanesulfonic acid), a glycine buffer system, and a carbonate buffer system.

17. The kit of claim 14, further comprising a detergent.

18. The kit of claim 17, wherein the detergent comprises a component of the aqueous solution.

19. The kit of claim 17, wherein the detergent is selected from the group consisting of sodium dodecyl sulphate, fatty acid salts, octyl glycoside, 3-[(3-cholamidopropyl)dimethylammonio]-1-propanesulfonate, sodium dodecyl maltoside, lauryldiethylamine oxide, NP-40, primary amines, amine acetates, hydrochlorides, quaternary ammonium salts, trimethylethyl ammonium bromide, amides of substituted diamines, diethanolaminopropylamine, diethylaminopropylamide, amides of cyclized diethylenetriamine, alkylaryl sulfonates, petroleum sulfonates, sulfonated glycerides, cholamides, sulfobetaines, alkyl glycosides, saponins, alkylpolyethylene glycol ethers, hydroxypolyethoxydodecane, (1,1,3,3-tetramethylbutyl)phenyl-polyethylene glycol, a-dodecyl-w-hydroxy-poly(oxy-1,2-ethanediyl)polyethylene glycol (23) monododecyl ether, polyoxyethylene 20 cetyl ether, polyoxyethylenesorbitan monolaurate, polyoxyethylenesorbitan monooleate, 4-nonylphneyl-polyethylene glycol, n-octyl-β-D-glucoside, and N-Methyl-N-octanoyl-D-glucamine.

20. The kit of claim 14, wherein the releasing agent is selected from the group consisting of EDTA, DTPA, EGTA, DTPMP and EDPMP.

* * * * *